US007854158B2

(12) United States Patent
Burns et al.

(10) Patent No.: US 7,854,158 B2
(45) Date of Patent: Dec. 21, 2010

(54) SYSTEMS AND METHODS FOR MEASUREMENT AND ANALYSIS OF PIPELINE CONTAMINANTS

(75) Inventors: David Burns, Mineral Wells, TX (US); Tomas Borjon, Millsap, TX (US); Mark Scott, Weatherford, TX (US)

(73) Assignee: Perry Equipment Corporation, Mineral Wells, TX (US)

( * ) Notice: Subject to any disclaimer, the term of this patent is extended or adjusted under 35 U.S.C. 154(b) by 2 days.

(21) Appl. No.: 11/646,846

(22) Filed: Dec. 28, 2006

(65) Prior Publication Data

US 2008/0156073 A1 Jul. 3, 2008

(51) Int. Cl.
*G01N 30/02* (2006.01)
*G01N 30/90* (2006.01)

(52) U.S. Cl. .................. 73/23.35; 73/23.41; 73/28.01; 73/28.04; 73/863.03; 73/863.51; 73/864.73

(58) Field of Classification Search ............... 73/23.35, 73/28.01, 28.04, 863.03, 863.51, 863.52, 73/874.73, 23.41
See application file for complete search history.

(56) References Cited

U.S. PATENT DOCUMENTS

| 3,794,909 | A | * | 2/1974 | Smith | 324/464 |
| 4,140,005 | A | * | 2/1979 | Kittelson | 73/28.02 |
| 4,413,533 | A | | 11/1983 | Diesel | 73/863.31 |
| 4,809,543 | A | | 3/1989 | Baillie | 73/61.1 |
| 5,040,890 | A | | 8/1991 | North, Jr. | 356/72 |
| 5,148,945 | A | * | 9/1992 | Geatz | 222/1 |
| 5,751,422 | A | | 5/1998 | Mitchell | 356/337 |
| 6,062,092 | A | * | 5/2000 | Weaver | 73/863.03 |
| 6,168,647 | B1 | | 1/2001 | Perry, Jr. et al. | 95/19 |
| 6,357,304 | B1 | * | 3/2002 | Mayeaux | 73/863.23 |
| 6,584,865 | B1 | | 7/2003 | Doherty et al. | 73/863.03 |
| 6,813,303 | B2 | | 11/2004 | Matsuda et al. | 372/75 |
| 7,024,867 | B2 | * | 4/2006 | Arman et al. | 62/6 |
| 2002/0007858 | A1 | * | 1/2002 | Xu et al. | 137/828 |
| 2003/0235926 | A1 | | 12/2003 | Knollenberg et al. | 436/181 |
| 2004/0079236 | A1 | * | 4/2004 | Welker | 96/413 |
| 2004/0139785 | A1 | * | 7/2004 | Abdul-Khalek | 73/28.01 |
| 2005/0151968 | A1 | | 7/2005 | Drake et al. | 356/338 |
| 2008/0156073 | A1 | | 7/2008 | Burns et al. | 73/23.35 |

* cited by examiner

*Primary Examiner*—Daniel S Larkin
(74) *Attorney, Agent, or Firm*—Chinh H. Pham; Greenberg Traurig LLP

(57) ABSTRACT

A system for measurement and analysis of pipeline contaminants is provided. The system includes a first assembly for engaging a pipeline from which a first fluid flow sample may be isokinetically collected for measurement of aerosol contaminants. The system also includes a second assembly for engaging the pipeline from which a second fluid flow sample may be collected for chromatographic analysis of the aerosol contaminants. The system may further include a third assembly for engaging the pipeline from which a fluid flow sample may be obtained for measurement of solid contaminants. Information on aerosol contaminants and solid contaminants can subsequently be used to select an appropriate extraction technology to control the presence of aerosol and solid contaminants within the pipeline. Information from the chromatographic analysis, on the other hand, may be used to identify the origin of the aerosol contaminants, so that corrective measures can be implemented to minimize the presence of aerosol contaminants within the pipeline. A method for measurement and analysis of pipeline contaminants is also provided.

29 Claims, 4 Drawing Sheets

SYSTEMS AND METHODS FOR MEASUREMENT AND ANALYSIS OF PIPELINE CONTAMINANTS

TECHNICAL FIELD

The present invention relates to systems and methods for measurement of contaminants, and more particularly, to the isokinetic sampling, measurement, and analysis of contaminants in a fluid flow within a pipeline to aid in the control of these contaminants.

BACKGROUND ART

Current commercially available gas turbines and other critical gas or fluid flow systems for use in connection with the energy industry can be extremely sensitive to contamination, such as, solid contaminants (i.e., particulates), liquid contaminants, and/or liquid aerosol, present within the process fluid flow. Solid contaminants, as an example, can act to wear rotating components, foul heat exchangers, contaminate cooling liquids, clog processing equipment, as well as affecting numerous other processing and equipment problems. Liquid contaminants, on the other hand, can accumulate or coalesce over time, and can, as the volume increases, travel along the sides and bottom of a pipeline and affect the efficiency of the fluid flow. Likewise, liquid aerosol or droplets, although small in mass, can similarly accumulate and build up over time, and have damaging effects on downstream equipment in the fluid flow system.

In order to minimize the occurrence of such contamination, filtration and separation equipment have been employed in connection with these fluid flow systems, so that contaminants present within the fluid flow can be removed therefrom. At present, most manufacturers have developed cleanliness requirement specifications for their fuel and feed gas flow systems. To accommodate such requirements, modern filters and separators have been designed to remove particulate contaminants with high efficiency. However, the issue with liquid contaminants or liquid aerosols may remain. Moreover, the selection of filtration and separation equipment that can provide adequate removal of the right contaminants can be a difficult task. In particular, there is available a number of filtration and separation equipment adapted for handling different contaminants in connection with different applications. As a result, unless there is knowledge about the contaminants within the fluid flow, as well as their characteristics, inadequate filtration and separation equipment may be selected, purchased and subsequently installed. The failure to employ optimal or at least appropriate filtration and separation equipment, in many instances, can lead to inadequate removal of the contaminants resulting in damage to downstream equipment. In addition, operational costs of the system can be significantly higher as a result of poor performance caused by insufficient removal of the contaminants.

Even if the appropriate filters and separators may be used, an additional verification step may be needed in order to assure that contamination within the fluid system is being adequately controlled. Presently, most testing of fluid flow contaminants within an energy industry pipeline is accomplished by collecting samples of the fluid flow for subsequent offsite analysis. However, in many instances, a substantially accurate sample may not be available, especially when the sample cannot be isokinetically collected. In other words, if fluid entering the sampling system does not exhibit similar velocity and kinetic energy to the fluid flow in the pressurized process fluid flow, an accurate representation of contaminants within the fluid flow may not be collected. Additionally, at present, the collected sample must either be mailed or transported to a third party laboratory where the sample sits and waits to be measured and analyzed. During this period, the sample can change and the contaminants can often be lost to the sample container. Furthermore, as a number of contaminants may be volatile in nature, and due to the time consuming approach of the present protocol, many of the contaminant samples never get sent off for analysis.

Those samples that do get tested, however, may be measured using, for instance, a particle analyzer or counter to determined the amount or level of the contaminants and thus the cleanliness of the fluid flow. Examples of particle analyzers include light scattering analyzers, e.g., laser beam, and condensation nucleus particle counters, either of which can be employed to detect the level of particulate contamination from collected samples within the process fluid flow. Nevertheless, regardless of how sensitive or accurate the analyzers or counter may be, since the collected samples may not be an adequate representation of the contaminants within the fluid flow, the subsequent analysis of the collected samples may not provide an accurate picture or a real time determination of the level of contaminants within the fluid flow.

Moreover, knowledge of the amount or level of contaminants does not necessarily help to identify the source of the contaminants. In certain instances, it may be important to know the make up or origin of the contaminants, so that appropriate measures may be implemented to control the source of the contaminants. For example, if the source of the contaminants might be from additive chemicals or lubricating oils, or simply due to unfavorable conditions within the pipeline, knowledge of the source or origin can help to minimize the generation of contaminants from such source or origin.

Since contaminants within a collected sample and contaminants within a fluid flow can almost always be different, it is desirable to provide an approach that permits relatively quick accurate sampling for the measurement and analysis of contamination data, which data can subsequently be used to select the optimal filtration and separation equipment in order to control the existence of contaminants within the fluid flow being analyzed.

SUMMARY OF THE INVENTION

The present invention provides, in one embodiment, a system for measurement and analysis of pipeline contaminants. The system includes a first assembly for engaging a pipeline and from which a first fluid flow sample may be obtained for measurement of aerosol contaminants. In an embodiment, the first assembly may be provided with a first assembly probe for extending into the pipeline for isokinetically collecting the fluid flow sample to ensure that a representative amount of contaminants within the pipeline can subsequently be measured. The first assembly may also be provided with a particle counter, in fluid communication with the probe, for measuring a number and size of aerosol particles within the fluid flow sample. The resulting information can subsequently be used to obtained a mass content of the aerosol particles, so as to permit a selection of an appropriate extraction technology to control the presence of aerosol contaminants within the pipeline. The system further includes a second assembly for engaging the pipeline and from which a second fluid flow sample may be obtained for chromatographic analysis of the aerosol contaminants. In an embodiment, a location on the pipeline to which the first assembly and the second assembly engage may be a same location. Alternatively, a location on the pipeline to which the first assembly and second assembly engage may be spatially situated from one another. The second assembly, in an embodiment, may be provided with a second assembly probe for extending into the pipeline for isokinetically collecting the fluid flow sample to ensure that a representative amount of aerosol contaminants within the pipeline can subsequently be analyzed. The second assembly may also be provided with a cylinder coupled to the second assembly probe for housing the fluid flow sample directed from the second assembly probe. A chromatograph may further be provided in fluid communication with the cylinder for determining constituents of the fluid flow sample in order to identify the origin of the aerosol contaminants. In that way, corrective measures can be implemented to minimize the presence of aerosol contaminants.

The present invention further provides a method for measurement and analysis of pipeline contaminants. In an embodiment, the method includes initially extending a first probe into a fluid flow within a pipeline, so that aerosol contaminants can subsequently be measured. Then, a first fluid flow sample may be isokinetically collected in the first probe. Next, the collected first fluid flow sample may be directed from the first probe into a particle counter. Thereafter a number and size of aerosol particles within the fluid flow sample may be measured within a particle counter. The resulting information can subsequently be used to obtained a mass content of the aerosol particles. Knowledge of the mass content can permit a selection of an appropriate extraction technology to control the presence of aerosol contaminants within the pipeline. The method further includes extending a second probe into the fluid flow within a pipeline, so that constituents of the fluid flow sample can subsequently be determined in order to identify the origin of the aerosol contaminants. In one embodiment, extending the second probe within the pipeline includes removing the first probe prior to extending the second probe into a same area of the pipeline. Alternatively, the first probe and second probe may be placed at locations spatially situated from one another. Next, the second fluid flow sample may be isokinetically collected in the second probe. In an embodiment, the isokinetically collected first fluid flow sample and second fluid flow sample may be collected substantially simultaneously with one another. Thereafter, the collected second fluid flow sample may be directed from the second probe into a chromatograph. In one embodiment, prior to directing the second fluid flow sample into the chromatograph, the second fluid flow sample may be stored in a cylinder. Constituents of the fluid flow sample may then be determined in order to identify the origin of the aerosol contaminants, so that corrective measures can be implemented to minimize the presence of aerosol contaminants.

The present invention further provides another method for measurement and analysis of pipeline contaminants. The method includes initially extending a first probe and a second probe into a fluid flow within a pipeline at locations spatially situated from one another, so that contaminants can subsequently be determined. Then, a first fluid flow sample and a second flow sample may be isokinetically collected substantially simultaneously in their respective probes. Next, the collected first fluid flow sample may be directed from the first probe into a particle counter, while the collected second fluid flow sample may be directed from the second probe into a chromatograph. In an embodiment, the collected second fluid flow sample may be stored in a cylinder prior to being directed to the chromatograph. Subsequently, a number and size of aerosol contaminants within the first fluid flow sample may be measured within the particle counter. This information can subsequently be used to obtained a mass content of the aerosol contaminants, so as to permit a selection of an appropriate extraction technology to control the presence of aerosol contaminants within the pipeline. Additionally, constituents of the second fluid flow sample may be determined in order to identify the origin of the aerosol contaminants, so that corrective measures can be implemented to minimize the presence of aerosol contaminants.

DESCRIPTION OF SPECIFIC EMBODIMENTS

Figures 1A, 1B:
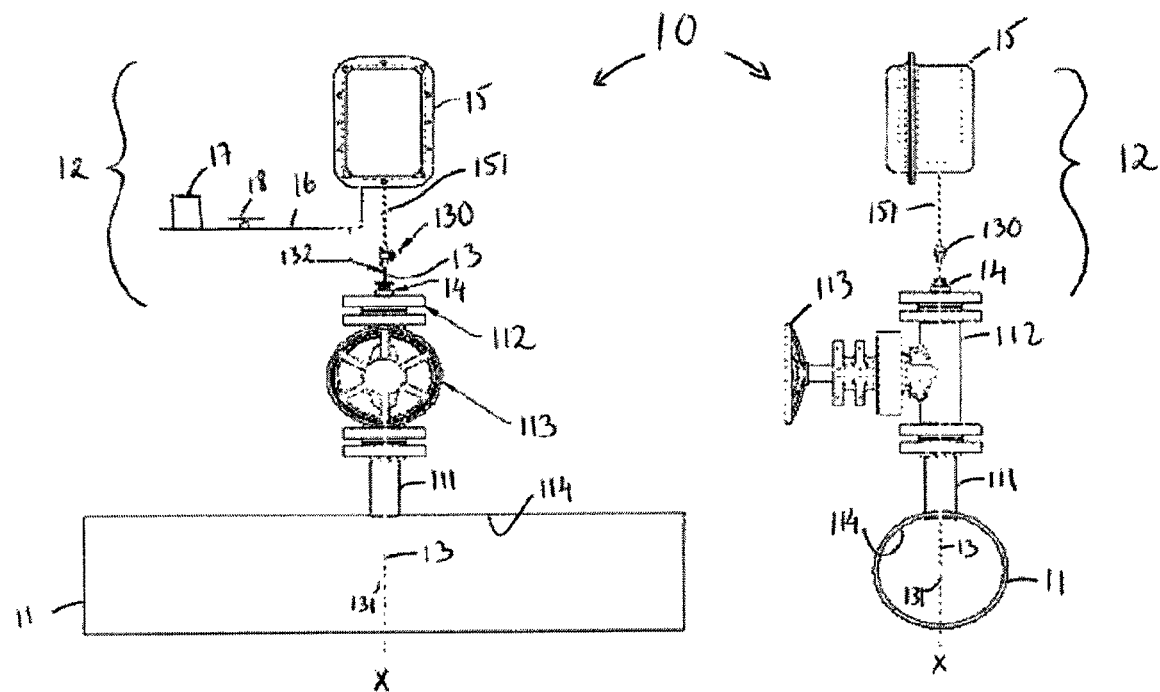
Figs. 1A-B illustrate an assembly for the direct measurement of contaminants in a fluid flow in accordance with one embodiment of the present invention.

With reference to FIGS. 1A-B, the present invention provides, in one embodiment, a system 10 for use in the measurement and analysis of contaminants within a fluid flow system, such as pipeline 11. System 10, in an embodiment, may include a contaminant measurement assembly 12 designed to engage pipeline 11 by way of a sampling nozzle 111. Nozzle 111, as illustrated, may be situated at any desired point along pipeline 11 and provides an opening through which assembly 12 may communicate with the fluid flow within pipeline 11. To prevent fluid flow from escaping through the sampling nozzle 111 when assembly 12 may not be in engagement therewith or when assembly 12 is not in use, sampling nozzle 111 may include a valve, such as isolation valve 112, which can be actuated between an open and closed position, for example, by way of wheel 113.

In accordance with one embodiment, assembly 12 includes a probe 13 designed for transporting a fluid sample from within the pipeline 11 to a contaminant measurement device, for instance, device 15. To that end, probe 13 may be made to extend from an exterior environment, across isolation valve 112, down through sampling nozzle 111, and into pipeline 11 where it may communicate with the fluid flow. To ensure optimal communication with the fluid flow within pipeline 11, probe 13 may be situated so that its tip 131 extends sufficiently into the fluid flow. In one embodiment, tip 131 may extend at least approximately 2.0 inches past wall 114 of pipeline 11. In addition, to ensure adequate measurement of contaminants within the fluid flow, probe 13 may be situated along pipeline 11 where the velocity of the fluid flow may be between about 1 ft/sec to about 60 ft/sec. In an embodiment, tip 131 of probe 13 may be situated substantially transversely to axis X of probe 13, and more particularly, substantially perpendicularly to axis X of probe 13. In this manner, tip 131 may be positioned substantially parallel to the direction of flow within pipeline 11, so as to optimize the flow of fluid into the tip 131 of probe 13. Although provided with a design shown in FIG. 1A, it should be noted that tip 131 may be provided with various other designs, for example, tip 131 may be cut at an angle, e.g., 45 degrees, so long as the position of tip 131 may be such that fluid flow can optimally enter probe 13, and probe 13 can isokinetically collect a sample of the fluid flow. As noted above, isokinetic sampling involves the collection of a fluid sample within probe 13 at a substantially similar fluid velocity as that exhibited by the fluid flow within the pipeline 11. By employing isokinetic sampling, a fluid sample can be collected with a contaminant level that is representative of the contaminant level along the pipeline 11.

Since probe 13 may be exposed to an inhospitable environment within pipeline 11, probe 13 may be made from a strong material that can withstand such an inhospitable environment. For instance, probe 13 may be made from stainless steel, such as 1/8 inch or 1/4 inch stainless steel tubing. Of course, other similar materials, e.g., metals, metal alloys, may be used, so long as those materials can withstand the inhospitable environment within pipeline 11.

Figure 2:
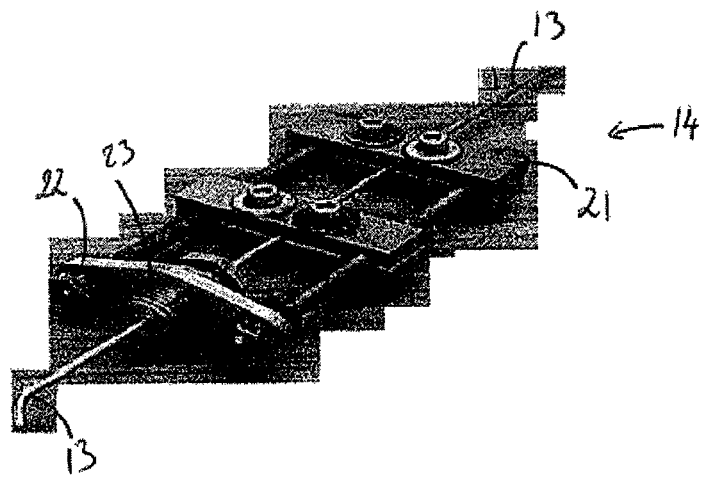
FIG. 2 illustrates a measurement probe for use in connection with the system shown in FIGS. 1A-C.

Assembly 12 may also include an insertion guide 14 to permit engagement between probe 13 and isolation valve 112 on sampling nozzle 111. In one embodiment, guide 14 may be similar to that shown in FIG. 2. Guide 14, in general, may include a body portion 21 through which probe 13 may extend. Body portion 21 may, in an embodiment, act to provide support to probe 13 and maintain the position (i.e., centering and elevation) of probe 13 within the sampling nozzle 111 and pipeline 11. Guide 14 may also include, towards its distal end 22, a coupling mechanism 23 to permit a secured engagement of the guide 14 to isolation valve 112 on sampling nozzle 111. In an embodiment, coupling mechanism 23 may be a threaded portion designed to be securely received within a complementary threaded opening (not shown) in isolation valve 112. Although illustrated as a threaded portion, coupling mechanism 23 may have other designs well known in the art, so long as such designs permit the coupling mechanism 23 to securely engage the isolation valve 112. In addition, guide 14 may be provided with any design, so long as the design can maintain the position of probe 13 within the sampling nozzle 111 and pipeline 11. To further ensure a tight-fitting engagement, in one embodiment, a seal (not shown), such as an O-ring or any other similar rubber or malleable seals, may be provided between coupling mechanism 23 and probe 13, so as to minimize any escape of fluid flow from the isolation valve 112.

Looking again at FIGS. 1A-B, assembly 12 may further include a valve, such as probe valve 130, situated at an outlet end 132 opposite tip 131 of probe 13. Probe valve 130, in one embodiment, can be actuated between an open position and a closed position to control the flow of fluid from within pipeline 11 out of probe 13 and into measurement device 15.

Assembly 12 may also include a pathway 16 coupled to measurement device 15 to permit the fluid flow to exit and be discharged from within the device 15. In one embodiment, a flow meter 17 may be situated along the pathway 16 in order to measure a rate (i.e., velocity) of fluid flow through assembly 12. Thus, if necessary, the fluid flow rate through assembly 12 can be adjusted and set to substantially match the rate of fluid flow within pipeline 11, so that an isokinetic sample may be collected within assembly 12 for contaminant measurement. Flow meter 17, in an embodiment, may be any commercially available flow meter capable of measuring fluid flow rate.

In order to adjust the rate of fluid flow through assembly 12, a flow valve 18 may be provided on pathway 16, for example, upstream of the flow meter 17 between measurement device 15 and flow meter 17. In one embodiment, flow valve 18 may be a needle-type valve that can be actuated between an open position and a closed position in order to change and set the rate of fluid flow, for instance, at isokinetic conditions.

Assembly 12, in an embodiment, may be designed to measure contaminants in the form of liquid aerosol. To that end, measurement device 15 may be a light scattering counter, such as any commercially available laser particle counter. Laser particle counter 15, as illustrated in FIGS. 1A-B, can include in inlet 151 through which fluid flow within probe 13 may be directed into particle counter 15. In one embodiment, inlet 151 may be designed to communicate with probe valve 130. For example, inlet 151 may be provided with a shape that can be complementarily received by probe valve 130. In such an instance, a seal (not shown) may be situated at a junction between inlet 151 and probe valve 130, so as to substantially eliminate or minimize any occurrence of fluid flow leakage therethrough. Alternatively, an adapter (not shown) may be provided between the probe valve 130 and inlet 151 to permit engagement between the probe valve 130 and inlet 151.

Laser particle counter 15, in an embodiment, may be a designed to receive an isokinetically collected fluid flow sample from pipeline 11 by way of probe 13, so as to ensure that a representative amount of contaminants within pipeline 11 may be measured. In addition, it should be noted that pipeline pressure and temperature may also be maintained within counter 15, as well as throughout assembly 12, so as not to vaporize or condense additional aerosol particles during the measurement.

As noted above, particle counter 15 may be any commercially available laser counter and general can be designed to receive a fluid flow sample. The fluid flow sample, once directed within the counter 15, may be permitted to flow through a particle measurement flow cell. A laser diode or any suitable light source, positioned within the counter 15 may transmit a beam of light through the flow cell. The beam of light may be directed through and perpendicular to the sampled fluid flow sample. Aerosol droplets or particles traveling through the fluid flow can act to scatter the beam of laser light. The scattered laser light can then be directed via mirrors or lens to a photo-analyzer. The photo-analyzer can thereafter process the light energy to electrical energy. The electrical pulse resulting from the particle scan be recorded as a particle with a corresponding size. In an embodiment, the particle size measurements may be diameter measurements of the substantially spherical aerosol particles or droplets. Generally, aerosol particles or droplets that exist in fluid flow within commercial gas pipelines can vary in size, and can range up to about 100 microns in diameter. The diameter measurements can subsequently be calculated to provide a corresponding a spherical volume. The spherical volume may next be converted to a mass by multiplying the liquid density by the spherical volume. The mass of all the particles measured over a certain period of time can then be summed and compared to the mass of the sampled fluid flow during the same period of time, thus providing an aerosol mass content measurement in the gas stream. This information may thereafter be used in determining the sizing and selection of liquid aerosol extraction technologies, e.g., filters, separator, such as Perry Equipment Corp.'s Gemini Purasep® (U.S. Pat. No. 6,168,647), and Perry Equipment Corp.'s vertical gas coalescers.

It should be appreciated that although disclosed in connection with a fluid flow pipeline 11, assembly 12 may be adapted for use with, for example, commercially available gas coalescers, either vertical or horizontal in design. When used in connection with such a coalescer, coupling of assembly 12 to the coalescer, in an embodiment, may be accomplished directly to the coalescer without the use, for example, of an isolation valve used in connection with a sampling nozzle in a pipeline.

Referring now to FIG. 3, the system 10, in addition to having the contaminant measurement assembly 12, may also include a chromatographic assembly 30 for use in determining the origin of the contaminants, such as aerosol particles, in the fluid flow. In that way, it can be determined whether the measured aerosols originated from liquid condensation or in the pipeline 11. The chromatographic measurement, in an embodiment, can be used to determined a dew point temperature of the fluid (i.e., gas). In particular, if the operating temperature of pipeline 11 is lower than the dew point temperature of the fluid, then condensation can be assumed to be the source of such aerosols.

In accordance with one embodiment, chromatographic assembly 30, similar to contaminant measurement assembly 12, may be designed to access the interior of pipeline 11 by way of a sampling nozzle 301, similar to sampling nozzle 111 in FIG. 1A. Such a sampling nozzle 301 may be situated at any desired point along pipeline 11 may, and in an embodiment, be nozzle 111 or may be spatially situated from nozzle 111. To the extent that sampling may be performed along a particular section of pipeline 11, and that particular section may be provided with only one sampling nozzle, assembly 12 may be removed from nozzle 111 and replaced with assembly 30 for the appropriated sampling and measurement. Otherwise, different sampling nozzles may be provided, such that each supports a different sampling and measurement assembly. As noted above, a valve, such as an isolation valve 302, may be provided in connection with the sampling nozzle 301 on pipeline 11 to open or close access to the fluid flow within pipeline 11, for example, by wheel 303.

Chromatographic assembly 30, in one embodiment, includes a probe 31, substantially similar to probe 13, designed to extract and transport a fluid sample from within the pipeline 11 to a collection cylinder 35 for subsequent chromatographic analysis. To that end, probe 31 may be made to extend across isolation valve 302, down through sampling nozzle 301, and into pipeline 11, where it may communicate with the fluid flow. To ensure optimal communication with the fluid flow within pipeline 11, probe 31 may be situated so that its tip 311 extends sufficiently into the fluid flow. Similar to tip 131 of probe 13, tip 311 may extend at least approximately 2.0 inches past the wall 114 of pipeline 11. In addition, to ensure adequate sampling of the fluid flow, probe 31 may be situated along pipeline 11 where the velocity of the fluid flow may be between about 1 ft/sec to about 60 ft/sec. As illustrated, tip 311 may be cut at an angle, e.g., 45 degrees so as to optimize the flow of fluid into tip 311. Of course tip 311 may be provided with other designs, for instance, one similar to the transverse position of tip 131 in probe 13. Regardless of the design, tip 311 should permit isokinetic sampling by probe 31 of fluid flow within pipeline 11.

Like probe 13, since probe 31 in assembly 30 may be exposed to an inhospitable environment within pipeline 11, probe 31 may be made from a strong material that can withstand such an inhospitable environment. For instance, probe 31 may be made from stainless steel tubing. Of course, other similar materials, e.g., metals, metal alloys, may be used, so long as those materials can withstand the inhospitable environment within pipeline 11.

Assembly 30 may also include an insertion guide 33 to permit engagement between probe 31 and an isolation valve, such as valve 302, on sampling nozzle 301. In one embodiment, guide 33 may include a body portion 34 through which probe 31 may extend. Body portion 34 may, in an embodiment, act to provide support to probe 31 and maintain the position (i.e., centering or elevation) of probe 31 within the sampling nozzle 301 and pipeline 11. In accordance with one embodiment, guide 33 may include a threaded section to allow guide 33 to be securely received within a complementary threaded opening (not shown) in the isolation valve 302. Other designs well known in the art may also be used, so long as such designs permit a secured engagement with the isolation valve. To further enhance a tight-fitting engagement, in one embodiment, a seal (not shown), such as an O-ring or any other similar rubber or malleable seals, may be provided between the guide 33 and the probe 31, so as to minimize any escape of fluid flow through the isolation valve 302.

Figure 3A:
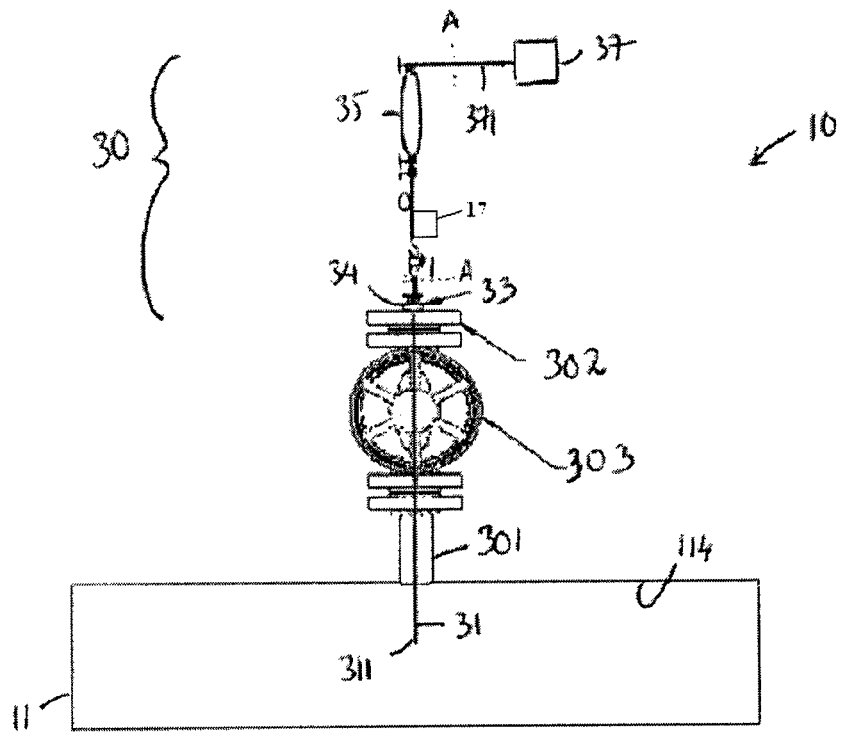
FIGS. 3A-B illustrate an assembly for analyzing the constituents of the fluid flow sampled in FIGS. 1A-C.
Figure 3B:
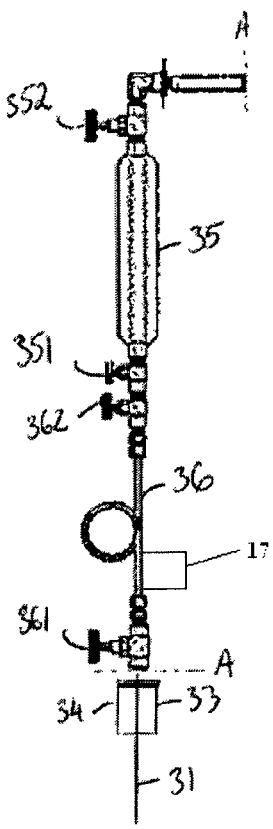

As shown in FIG. 3A, assembly 30, taken along line A-A, further includes a collection cylinder 35 in communication with probe 31. Cylinder 35, in an embodiment, may be a pressure vessel which can house a collected fluid sample from pipeline 11 for subsequent chromatographic analysis. Cylinder 35 may include valves 351 and 352 at opposite ends to control the ingress and egress of collected fluid sample into cylinder 35. An example of a cylinder for use in connection with the present invention includes a Standard Sample Cylinder from companies like Welker Engineering Company of Sugar Land, Tex.

In accordance with one embodiment of the present invention, a conduit 36 may be positioned between cylinder 35 and probe 31 to control the flow of the collected fluid sample into the cylinder 35. In particular, conduit 36 may be provided with a first valve 361 at an end adjacent guide 33 for controlling the flow of the collected fluid from probe 31 into conduit 36. Conduit 36 may also be provided with a second valve 362 at an opposite end adjacent valve 351 of cylinder 35. Valve 362, in an embodiment, may be used to purge fluid flow from within probe 31. Specifically, in certain instances, probe 31 may contain remnants of a fluid sample from a previous collection that may interfere with the present collection. To purge the previous fluid sample from probe 31, valve 362 may be actuated so that a volume of fluid flow from within pipeline 11 may be exhausted from probe 33 prior to collection.

To analyze the collected fluid flow sample within cylinder 35, assembly 30 may include a chromatograph, such as gas chromatograph 37, in fluid communication with cylinder 35. In one embodiment, a pathway 371 may be placed between valve 352 and chromatograph 37, so that upon actuation of valve 352, collected fluid flow sample may be released from within cylinder 35 and directed into the gas chromatograph 37 for chromatographic analysis.

Alternatively, once collected within cylinder 35, the cylinder 35 may be disengaged from assembly 30 and coupled to chromatograph 37 located in a lab, e.g., a mobile lab on-site or an off-site lab, for chromatographic analysis.

Chromatograph 37, in an embodiment, may be any commercially available chromatograph capable of identifying the constituents of the sampled fluid flow. For example, one such chromatograph may be the CP-4900 Micro-GC from Varian, Inc. in Palo Alto, Cali. In general, a chromatograph is an instrument that utilizes packed column technology to separate a fluid (e.g., gas) or a mixture into its constituents for subsequent analysis. By employing chromatographic analysis, the existence and amount of each constituent in the sampled fluid flow can be determined. In addition, since the concentration of each of the constituents can have an effect on, for instance, a final heat valve or quality of the fluid, knowledge of these concentrations can assist in the tuning of, for example, turbine engines for efficient operations and emissions control. The data on the constituents obtained from an analysis provided by a chromatograph may also used to model a hydrocarbon dew point of a fluid flow system. In an embodiment, the dew point information may be used to verify the origin of the liquid aerosol contaminants in system 10.

The hydrocarbon dew point can be an important physical property of the fluid flow system, such as a natural gas system, that should be determined prior to the design or implementation of fluid conditioning equipment. For instance, if the fluid temperature is below the hydrocarbon dew point, then liquid aerosols may form as liquids condense out of the fluid. Knowing this permits the appropriate filtration and/or separation technology to be implemented. On the other hand, if the fluid is at or below its dew point, then the fluid may have to be heated to keep, for instance, the liquid aerosol particles in solution as a vapor. It may also be common for pipelines that operate close to the hydrocarbon dew point to require insulation and heat tracing (external pipeline heating) to keep, for example, the cool morning air from producing unwanted liquids in the pipeline.

Figure 1C:
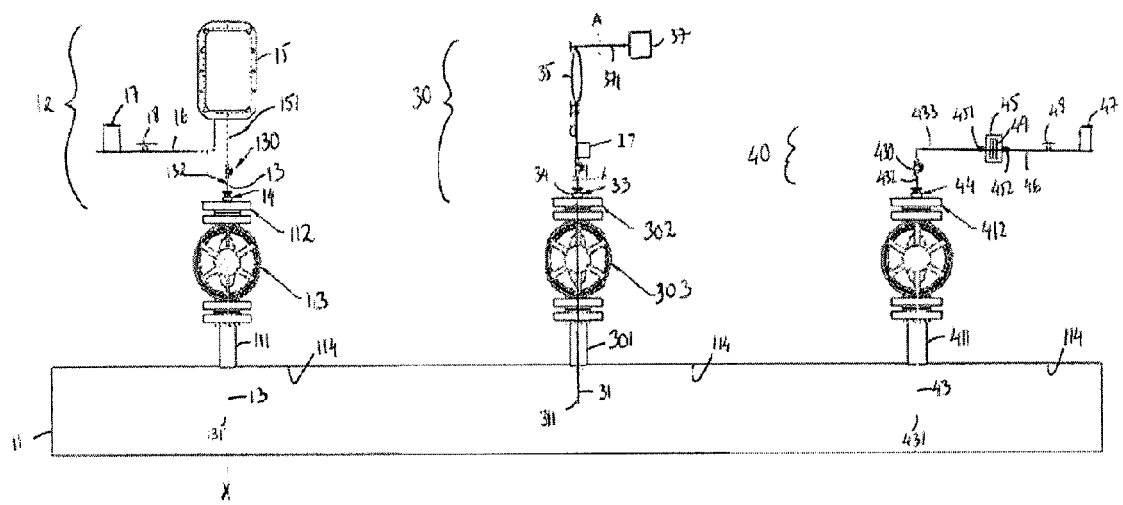
FIG. 1C illustrates various assemblies of the present invention being used along a pipeline, in accordance with an embodiment of the present invention.
Figure 4:
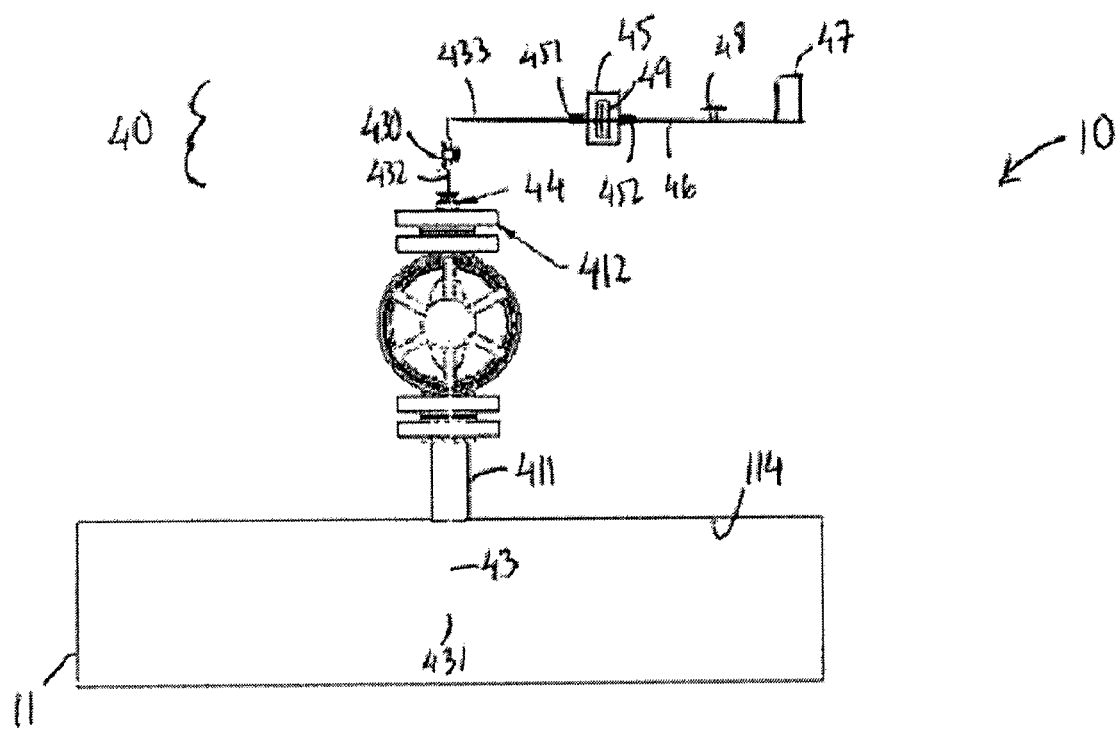
FIG. 4 illustrates another assembly for the measurement of contaminants in a fluid flow in accordance with one embodiment of the present invention.

With reference now to FIG. 4, to the extent that collection and measurement of solid particle contaminants may be needed, system 10 may also be provided with an additional contaminant measurement assembly, such as solids measurement assembly 40. Assembly 40, in an embodiment may be substantially similar to assembly 12 in FIG. 1, except that instead of having a particle counter 15, assembly 40 may be provided with a filter housing 45 for collecting solid contaminants from the fluid flow.

In order to avoid repetition and for ease of discussion, description of assembly 40 will now be made with the understanding that the components of assembly 40 may be substantially similar to those components in assembly 12, with the exception of filter housing 45. Like assembly 12, assembly 40 may be designed to engage pipeline 11 by way of a sampling nozzle 411 and isolation valve 412, which can be actuated between an open and closed position to prevent fluid flow from escaping through the sampling nozzle 411 when assembly 40 may not be in engagement therewith or when assembly 40 is not in use.

Assembly 40 may also include a probe 43 designed to transport a fluid sample from within the pipeline 11 to filter housing 45. To that end, probe 43 may be made to extend from an exterior environment, across isolation valve 412, down through sampling nozzle 411, and into pipeline 11 where it may communicate with the fluid flow. Probe 43, in an embodiment, may include a tip 431 provided with a design similar to that shown in FIG. 1A in connection with tip 131 of probe 13. Nevertheless, it should be appreciated that tip 431 may be provided with various other designs, for example, tip 431 may be cut at an angle, e.g., 45 degrees, so long as the position of tip 431 may be such that fluid flow within pipeline 11 can optimally enter probe 43 to permit isokinetic collection of a sample of the fluid flow. Since probe 43, like probe 13, may be exposed to an inhospitable environment within pipeline 11, probe 43 may be made from a strong material that can withstand such an inhospitable environment. For instance, probe 13 may be made from metals, such as stainless steel, metal alloys, or any other materials that can withstand the inhospitable environment within pipeline 11.

Assembly 40 may further include an insertion guide 44 to permit engagement between probe 43 and isolation valve 412 on sampling nozzle 411. In one embodiment, guide 44 may be similar to guide 14 shown in FIG. 2. Guide 44, in general, acts to provide support to probe 43 and maintain the position (i.e., centering and elevation) of probe 43 within the sampling nozzle 411 and pipeline 11. Guide 44 may also act to provide probe 43 with a secured engagement with isolation valve 412 on sampling nozzle 411. To further ensure a tight-fitting engagement, in one embodiment, a seal (not shown), such as an O-ring or any other similar rubber or malleable seals, may be provided between a coupling mechanism, similar to item 23 in FIG. 2, and isolation valve 412, so as to minimize any escape of fluid flow through the isolation valve 412.

In addition to the above, assembly 40 can also include a valve, such as probe valve 430, situated at an outlet end 432 opposite tip 431 of probe 43. Probe valve 430, in one embodiment, can be actuated between an open position and a closed position to control the flow of fluid from within pipeline 11 out of probe 43 and into filter housing 45.

Assembly 40 may further include a pathway 46 coupled to filter housing 45 to permit the fluid flow to exit and be discharged from within the housing 45. In an embodiment, a flow meter 47 may be situated along the pathway 46 in order to measure a rate of fluid flow through assembly 40. If necessary, the fluid flow rate through assembly 40 can be adjusted by flow valve 48 and set to substantially match the rate of fluid flow within pipeline 11, so that an isokinetic sample may be directed through assembly 40 for collection. In an embodiment, flow valve 48 may be situated between flow meter 47 and filter housing 45.

Assembly 40, as noted above, may be designed to collect solid contaminants for subsequent measurement by way of filter housing 45. To that end, filter housing 45 may be provided, in one embodiment, with an inlet 451 designed to be in fluid communication with probe valve 430. If necessary, a passageway 433 my be positioned between probe valve 430 and inlet 451 of filter housing 45, so that the sampled fluid flow may be directed therethrough to filter housing 45. Filter housing 45 may also be provided with an outlet 452 coupled to pathway 46 to discharge the sampled fluid flow from the housing 45 into pathway 46. In order to minimize fluid flow leakage at a juncture between each of the inlet 451 and outlet 452 with the respective probe valve 430 and pathway 46, a seal (not shown), such as a Swagelok® fitting, may be situated at such a juncture.

Figure 5:
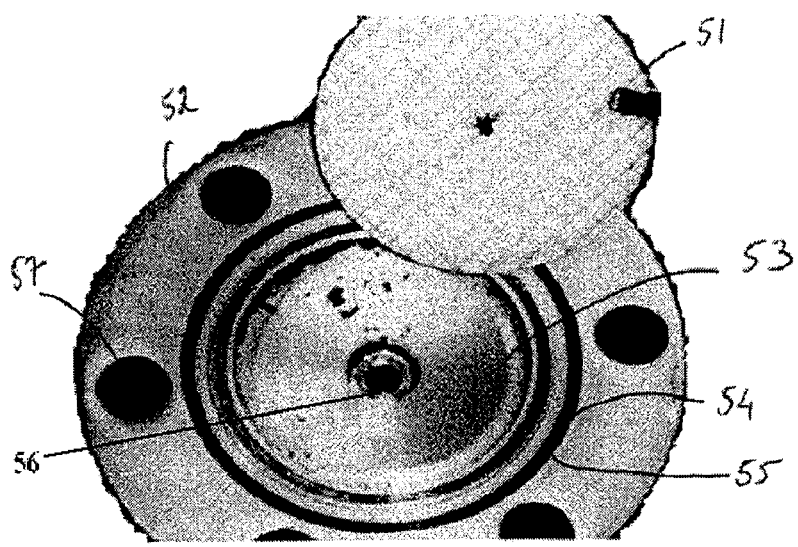
FIG. 5 illustrates a filter disk for use in connection with the system shown in FIG. 4.

Filter housing 45 may also include a chamber 49 within which a filter element 51 (FIG. 5) may be situated for collection of solid contaminants. To access chamber 49 for placement or replacement of a filter element 51, filter housing 45, looking at FIG. 5, may be designed, in an embodiment, to include opposing portions 52 capable of engaging and being separated from one another. Each portion 52, as shown in FIG. 5, may include a recess 53 designed to form chamber 49 when the two opposing portions 52 engage one another. To the extent desired, a seal, for example, an O-ring 54, may be positioned circumferentially about chamber 49 to provide chamber 49 with a substantially tight seal. In one embodiment, to retain seal 54 about chamber 49, complementary channels 55 may be provided about each recess 53, so that a portion of seal 54 may be situated within one channel 55 with the remaining portion of seal 54 being received within the other channel 55.

To permit fluid communication between each recess 53 and the respective inlet 451 or outlet 452, each portion 52 may be provided with an opening 56 at a juncture between recess 53 and the respective inlet 451 or outlet 452. Moreover, since substantially high pressure may be directed through filter housing 45 during collection of a fluid flow sample, in order to retain engagement of portions 52 against one another, filter housing 45 may be provided with an engagement mechanism capable of withstanding the substantially high pressure. In one embodiment, each portion 52 may be provided with complementary apertures 57 that may be in substantial alignment with one another and may be capable of receiving, for example, nuts and bolts, screws, or any other similar components therethrough. Of course, portions 52 may be provided with other designs, so that the portions 52 may be retained against one another. For instance, the use of clamps, buckles or another mechanisms known in the art may be employed.

Filter element 51, in an embodiment, may be in a shape that permits it to be received within chamber 49. In the embodiment shown in FIG. 5, filter element 51 be circular in shape, e.g., disc shape. However, it should be noted that filter element 51 may be provided with any geometric shape, so long as it can be received within chamber 49. To adequately collect solid contaminants, filter element 51, in accordance with one embodiment of the present invention, may be made from a piece of, for example, produced nylon with sufficient porosity to allow gas or liquid to flow therethrough, while allowing solid contaminants to be captured thereon. As conditions within pipeline 11 may vary from pipeline to pipeline, the porosity of filter element 51 may need to change, for instance, in diameter, in number, or both, in order to adequately meet the sampling conditions. Filter element 51, upon completion of the sampling, may be removed from the filter housing 45 for subsequent measurement and analysis of the collected solid contaminants.

Since the difference between assembly 40 and assembly 12 resides essentially in contaminant measurement device, that is, assembly 12 has particle counter 15 and assembly 40 has filter housing 45, to the extent desired, housing 45 along with filter element 51 therein may, in one embodiment of the present invention, be substituted for particle counter 15 in assembly 12. In other words, particle counter 15 may be removed from assembly 12 and replaced with filter housing 45, or vice versa. Such an approach may be employed in the event a particular section of pipeline 11 may not have a sufficient number of sampling nozzles. Of course, pipeline 11 may be provided a sufficient number of sampling nozzles, so that assembly 12 and assembly 40 may each engage an independent sampling nozzle, as may also be the case with assembly 30 for chromatographic analysis.

In operation, depending of the type of measurement to be taken, each, some, or all of the assemblies discussed above in connection with system 10 may be used. However, prior to activating the assembly, each assembly may initially need to be set up along pipeline 11 before measurement of the fluid flow can take place. In particular, prior to engaging the assembly to a sampling nozzle, fluid flow velocity may initially be calculated along a section of pipeline where a sample fluid flow may be collected for measurement, to see whether the velocity may be within an appropriate range. In an embodiment, the fluid flow velocity appropriate for measurement may range from about 1 ft/sec to about 60 ft/sec. If the fluid flow velocity is within the appropriate range, in an embodiment, an insertion guide, such as guide 14 may be inserted into isolation valve 112 and tighten therewith.

It should be noted that reference herein will be made in connection with assembly 12 and its components. However, since assembly 30 and assembly 40 may have substantially similar components to assembly 12, it should be understood that the description herein of assembly 12 may also be applicable to assemblies 30 and 40.

Next, probe 13 may be inserted through the tightened guide 14, across isolation valve 112, into sampling nozzle 111, and into the fluid flow. In an embodiment, tip 131 of probe 13 may be placed at least approximately 2.0 inches past a juncture between the sampling nozzle 111 and pipeline 11. Then, if necessary, probe valve 130 may be actuated into an open position to purge (i.e., clean) probe 13 of unwanted fluids, particles, or other components. Thereafter, contaminant measurement device, such as laser counter 15, may be attached to the probe 13, along with the flow meter 17, and associated pathway 16. Using the flow meter 17, the velocity of fluid flow through assembly 12 may be determined. To the extent needed, flow valve 18 may be adjusted in order to change and set the velocity of fluid flow at, for instance, isokinetic conditions. Subsequently, fluid flow within the pipeline 11 may be directed into tip 131 and allowed to travel along the probe 13, across probe valve 130, through inlet 151 of laser counter 15, and into laser counter 15. Laser counter 15, having been activated, may then perform a particle count and a measurement of particle size present in the fluid flow. Based on data obtained for the count and size, the mass of the particles measured over a certain period of time can then be calculated and compared to the mass of the sampled fluid flow during the same period of time. The difference between the two calculated masses can thus provide an aerosol mass content measurement in the gas stream. This information may thereafter be used in determining the sizing and selection of liquid aerosol extraction technologies.

During or subsequent to the measurement by assembly 12, assembly 30 may be activated along pipeline 11, so that the origin of the contaminants, such as aerosol particles measured by assembly 12, may be identify by chromatographic analysis. In that way, should the contaminants originate from, for instance, chemicals or lubricating oils added to the pipeline during the compression, dehydration or treating stage of the process, or from the fluid flow itself, corrective measures can be implemented. As noted above, prior to activating assembly 30, a set up process similar to that provided for assembly 12 may be implemented.

A sample of fluid flow may be isokinetically collected within cylinder 35 by directing fluid flow in the pipeline into tip 311 and allowed to travel along the probe 31, through conduit 36, across valve 351 of cylinder 35, and into cylinder 35. Once collected within cylinder 35, the fluid flow sample may be directed into the gas chromatograph 37 for chromatographic analysis. Directing the collected sample from cylinder 35 into chromatograph 37 may be accomplished by way of pathway 371. Alternatively, cylinder 35 may be disengaged from assembly 30 and coupled to chromatograph 37 located in a lab, e.g., a mobile lab on-site or an off-site lab, for chromatographic analysis.

Data on the constituents obtained from an analysis provided by a chromatograph may be used to determine the existence and amount of each constituent in the sampled fluid flow, so as to permit identification of the origin of the contaminants within the fluid flow system. The data may also be used to model a hydrocarbon dew point of a fluid flow system. The hydrocarbon dew point can be an important physical property of the fluid flow system, since if the fluid temperature is below the hydrocarbon dew point, then liquid aerosols may form as liquids condense out of the fluid. Knowing this permits the appropriate filtration and/or separation technology to be implemented. On the other hand, if the fluid flow is at or below its dew point, then the fluid flow may have to be heated to keep, for instance, the liquid aerosol particles in solution as a vapor.

To the extent desired, assembly 40 may also be activated along pipeline 11 to isokinetically collect a fluid flow sample and thereafter measured for the representative presence of solid contaminants within pipeline 11. Again, as noted above, prior to activating assembly 40, a set up process similar to that provided for assembly 12 may be implemented.

In one embodiment, fluid flow within pipeline 11 may be directed into tip 431 and allowed to travel along probe 43, across probe valve 430, through inlet 451 of filter housing 45, into filter housing 45, and across filter element 51 in housing 45. Filter element 51, because of its porosity, can allow the fluid flow to move across the filter element 51, while capturing solid contaminants thereon. Thereafter, filter element 51 may be removed from housing 45 and the collected contaminated measured. In one embodiment, the filter element 51 may be placed within a dehydration oven in order to evaporate moisture from the filter element 51. It should be appreciated that the filter element 51 should be substantially free of moisture in order to provide optimal mass measurement. Moreover, should it be desired, filter element 51 may be placed on a Petri dish when placed within the dehydration oven. Next, filter element 51 may be removed from the dehydration oven and allowed to cool in a desiccator vat. The desiccator vat may simply be a pot with a lid having a desiccate-like silica gel. Allowing the filter element 51 to cool to room temperature in the desiccator vat can keep the filter element 51 from re-absorbing moisture from the air.

The filter element 51 may then be weighed on a scale and its mass with the collected solid contaminants compared against its previously measured mass without the collected solid contaminants. Additionally, the filter element 51 or its photo may be viewed under a counting microscope to determine the number and size of the solid particles in order to provide a particle size distribution for the sample. These data can then be used to select the appropriate filtration and separation technology for implementation in connection with the fluid flow system.

As noted above, system 10 may be designed to permit assembly 12 to be used simultaneously with assembly 30, or to permit assembly 12 to be used simultaneously with assembly 40 and assembly 30. Alternatively, if only one sampling nozzle is provided, each assembly may be used in succession and in any combination as provided above. Moreover, since the assemblies share a variety of common features, including the guide, and probe, in one embodiment, it is contemplated that, for example, the particle counter 15 in assembly 12 can be removed and replaced with cylinder 35 and chromatograph 37 of assembly 30 or replaced with filter housing 45 of assembly 40, depending on which assembly needs to be employed. Likewise, probe 13, probe 31, and probe 43 may be used interchangeably among the various assemblies. Of course, should it be desired, only one probe may be provided for use with all the assemblies. In such an embodiment, the probe may be removed from one assembly after sampling and coupled to another assembly for a subsequently sampling of the fluid flow in pipeline 11.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains.

What is claimed is:

1. A system for measurement and analysis of pipeline contaminants, the system comprising:
    (a) a first assembly for engaging a pipeline from which a fluid flow sample may be obtained for measurement of aerosol contaminants, the first assembly having:
        a first assembly probe having a substantially uniform diameter along its length for extending into the pipeline for isokinetically collecting the fluid flow sample to ensure that a representative amount of contaminants within the pipeline can subsequently be isokinetically measured; and
        a particle counter in fluid communication with the probe for measuring a number and size of aerosol particles within the fluid flow sample, which information can subsequently be used to obtained a mass content of the aerosol particles, so as to permit a selection of an appropriate extraction technology to control the presence of aerosol contaminants within the pipeline; and
    (b) a second assembly for engaging the pipeline from which a fluid flow sample may be obtained for chromatographic analysis of the aerosol contaminants, the second assembly having:
        a second assembly probe having a substantially uniform diameter along its length for extending into the pipeline for isokinetically collecting the fluid flow sample to ensure that a representative amount of aerosol contaminants within the pipeline can subsequently be isokinetically analyzed;
        a cylinder coupled to the second assembly probe for housing the fluid flow sample directed from the second assembly probe; and
        a chromatograph in fluid communication with the cylinder for determining constituents of the fluid flow sample in order to identify the origin of the aerosol contaminants, so that corrective measures can be implemented to minimize the presence of aerosol contaminants.

2. A system as set forth in claim 1, wherein each of the first assembly probe and second assembly probe includes a tip designed to optimize the flow of fluid within the pipeline into the probe.

3. A system as set forth in claim 1, wherein the particle counter is a light scattering counter.

4. A system as set forth in claim 1, wherein each of the first assembly and second assembly further includes a flow meter for measuring fluid flow velocity through the each of the respective assembly.

5. A system as set forth in claim 1, wherein the fluid flow collected by the first probe and the second probe has a velocity that ranges from about 1 ft/sec to about 30 ft/sec.

6. A system as set forth in claim 1, wherein each of the first assembly and the second assembly is designed to engage the pipeline at a same location in succession.

7. A system as set forth in claim 1, wherein each of the first assembly and the second assembly engages the pipeline spatially situated from one another.

8. A system as set forth in claim 1, further including a third assembly for engaging the pipeline from which a fluid flow sample may be obtained for measurement of solid contaminants, the third assembly having:
    a third assembly probe for extending into the pipeline for isokinetically collecting the fluid flow sample to ensure that a representative amount of contaminants within the pipeline can subsequently be measured;
    a filter housing in fluid communication with the probe for receiving the fluid flow sample from the probe; and
    a filter element positioned within the filter housing through which the fluid flow sample can be directed, so that solid contaminants can be collected thereon for subsequent calculation of the collected mass to permit a selection of an appropriate extraction technology to control the presence of solid contaminants within the pipeline.

9. A system as set forth in claim 8, wherein the filter housing includes a chamber within which the filter element can be positioned.

10. A system as set forth in claim 8, wherein the filter element is provided with a porosity sufficient to permit fluid flow to pass therethrough, while allowing solid contaminants to be captured thereon.

11. A system as set forth in claim 8, wherein the third assembly further includes a flow meter for measuring fluid flow velocity through the third assembly.

12. A system as set forth in claim 8, wherein a location on the pipeline to which the third assembly engages is the same location that the first assembly and the second assembly engage.

13. A system as set forth in claim 8, wherein a location on the pipeline to which the third assembly engages is spatially situated from each of the locations that the first and the second assembly engages.

14. A system as set forth in claim 1, wherein each of the first assembly probe and second assembly probe includes a tip situated substantially transverse to an axis of the respective probe.

15. A system as set forth in claim 1, wherein each of the first assembly and second assembly further includes a guide through which a probe may extend, so as to maintain the probe in a substantially centering or elevated position within the pipeline.

16. A method for measurement and analysis of pipeline contaminants, the method comprising:
   extending into a fluid flow within a pipeline, a first probe having a substantially uniform diameter along its length so that aerosol contaminants can subsequently be isokinetically measured;
   isokinetically collecting a first fluid flow sample in the first probe;
   directing the collected first fluid flow sample from the first probe into a particle counter;
   isokinetically measuring within the particle counter a number and size of aerosol particles within the fluid flow sample, which information can subsequently be used to obtain a mass content of the aerosol particles, so as to permit a selection of an appropriate extraction technology to control the presence of aerosol contaminants within the pipeline;
   extending into the fluid flow within the pipeline, a second probe having a substantially uniform diameter along its length so that constituents of the fluid flow sample can subsequently be isokinetically determined in order to identify the origin of the aerosol contaminants;
   isokinetically collecting a second fluid flow sample in the second probe;
   directing the collected second fluid flow sample from the second probe into a chromatograph; and
   isokinetically determining the constituents of the fluid flow sample in order to identify the origin of the aerosol contaminants, so that corrective measures can be implemented to minimize the presence of aerosol contaminants.

17. A method as set forth in claim 16, wherein the steps of extending a first probe and second probe include positioning a tip of the respective probe within an area of the pipeline having adequate fluid flow and sufficient fluid flow velocity.

18. A method as set forth in claim 16, wherein the step of extending a second probe includes removing the first probe from within the pipeline prior to extending the second probe into a same area of the pipeline.

19. A method as set forth in claim 16, wherein the steps of extending a first probe and second probe include placing the respective probes at locations spatially situated from one another.

20. A method as set forth in claim 16, wherein the steps of isokinetically collecting a first fluid flow sample and second fluid flow sample include adjusting the fluid flow in the respective probe to match the fluid flow within the pipeline.

21. A method as set forth in claim 16, wherein the steps of isokinetically collecting a first fluid flow sample and second fluid flow sample include substantially simultaneously collecting the first fluid flow sample and the second fluid flow sample.

22. A method as set forth in claim 16, wherein the step of directing the collected second fluid flow sample includes storing the sample within a cylinder in communication with the second probe prior to directing the sample into the chromatograph.

23. A method as set forth in claim 16, further including:
   extending a third probe into the fluid flow within the pipeline, so that solid contaminants can subsequently be measured;
   isokinetically collecting a third fluid flow sample in the third probe;
   directing the collected third fluid flow sample from the third probe into a filter housing and across a filter element therein; and
   collecting solid contaminants onto the filter element and subsequently calculating a collected mass thereon to permit a selection of an appropriate extraction technology to control presence of solid contaminants within the pipeline.

24. A method as set forth in claim 23, wherein the step of extending a third probe includes removing either the first probe or the second probe from within the pipeline prior to extending the third probe into a same area of the pipeline.

25. A method as set forth in claim 23, wherein the step of extending a third probe includes placing the third probe at a location spatially situated from each of the first probe and second probe.

26. A method as set forth in claim 23, wherein the step of isokinetically collecting a third fluid flow sample includes substantially simultaneously collecting the third fluid flow sample with the first fluid flow sample and the second fluid flow sample.

27. A method for measurement and analysis of pipeline contaminants, the method comprising:
   extending into a fluid flow within a pipeline a first probe and a second probe, each having substantially uniform diameters along its length, at locations spatially situated from one another, so that contaminants can subsequently be isokinetically determined;
   isokinetically collecting substantially simultaneously a first fluid flow sample in the first probe and a second flow sample in the second probe;
   directing the collected first fluid flow sample from the first probe into a particle counter and the collected second fluid flow sample from the second probe into a chromatograph;
   isokinetically measuring within the particle counter a number and size of aerosol contaminants within the first fluid flow sample, which information can subsequently be used to obtained a mass content of the aerosol contaminants, so as to permit a selection of an appropriate extraction technology to control the presence of aerosol contaminants within the pipeline; and
   isokinetically determining constituents of the second fluid flow sample within the chromatograph in order to identify the origin of the aerosol contaminants, so that corrective measures can be implemented to minimize the presence of aerosol contaminants.

28. A method as set forth in claim 27, wherein the step of directing the collected second fluid flow sample includes storing the sample within a cylinder in communication with the second probe prior to directing the sample into the chromatograph.

29. A method as set forth in claim 27, further including:
extending a third probe into the fluid flow within the pipeline at a location spatially situated from that of the first probe and second probe;
isokinetically collecting a third flow sample in the third probe substantially simultaneously with the first and second fluid flow samples;
directing the third fluid flow sample from the third probe into a filter housing and across a filter element therein; and
collecting solid contaminants onto the filter element and subsequently calculating a collected mass thereon to permit a selection of an appropriate extraction technology to control presence of solid contaminants within the pipeline.

* * * * *